United States Patent [19]
Hussein et al.

[11] Patent Number: 5,298,238
[45] Date of Patent: Mar. 29, 1994

[54] LIQUID ORAL COMPOSITIONS COMPRISING DETERPENATED AND FRACTIONATED FLAVOR OILS

[75] Inventors: Mamoun M. Hussein, Mountain Lakes; Shirley A. Barcelon; Edward J. Carlin, Secaucus, all of N.J.

[73] Assignee: Warner-Lambert Company, Morris Plains, N.J.

[21] Appl. No.: 790,620

[22] Filed: Nov. 7, 1991

[51] Int. Cl.$^5$ .......................... A61K 7/16; A61K 7/26
[52] U.S. Cl. .......................................... 424/49; 424/58
[58] Field of Search ................................... 424/49–58

[56] References Cited

U.S. PATENT DOCUMENTS

| | | | |
|---|---|---|---|
| 3,164,524 | 1/1965 | Fund et al. | 167/93 |
| 3,492,131 | 1/1990 | Schlatter | 99/141 |
| 3,867,262 | 2/1975 | Rockland et al. | |
| 4,476,142 | 10/1984 | Netherwood et al. | 426/3 |
| 4,478,864 | 10/1984 | Blackwell et al. | 426/534 |
| 4,663,154 | 5/1987 | Ryan | 424/54 |
| 4,824,570 | 4/1989 | Bethvel et al. | 210/511 |
| 4,945,087 | 7/1990 | Talwar et al. | 514/60 |
| 5,030,459 | 7/1991 | Barcelon et al. | 426/3 |

FOREIGN PATENT DOCUMENTS

| | | | |
|---|---|---|---|
| 217719 | 4/1987 | European Pat. Off. | 424/58 |
| 113988 | 7/1988 | European Pat. Off. | 424/58 |
| 427505 | 5/1991 | European Pat. Off. | 424/58 |
| 0543155 | 9/1984 | France | 424/58 |
| 87/01299 | 3/1987 | PCT Int'l Appl. | |
| 89/00187 | 1/1989 | PCT Int'l Appl. | 424/58 |
| 91/13135 | 9/1991 | PCT Int'l Appl. | 424/58 |
| 656529 | 7/1986 | Switzerland | 424/58 |
| 1212360 | 11/1970 | United Kingdom | 424/58 |

OTHER PUBLICATIONS

Jacobs "Flavoring Mouth Washes" Am Perf. & Essential oil Review 61(6)469 471 Jun. 1953.

*Primary Examiner*—Shep K. Rose
*Attorney, Agent, or Firm*—Andrea Ryan

[57] ABSTRACT

Liquid oral compositions comprising a liquid carrier and one or more deterpenated and fractionated flavor oil(s) have improved taste and clarity.

5 Claims, No Drawings

LIQUID ORAL COMPOSITIONS COMPRISING DETERPENATED AND FRACTIONATED FLAVOR OILS

BACKGROUND OF THE INVENTION AND INFORMATION DISCLOSURE

Liquid oral compositions, such as a mouthwash, mouth rinse, oral spray, cough syrups and the like, typically contain flavor oils for imparting acceptable taste and mouthfeel characteristics. These compositions typically comprise a water, alcohol or water-alcohol carrier into which the flavor oils are dissolved or emulsified. The flavor oils normally include essential oils, such as peppermint oil, spearmint oil, eucalyptus oil, etc . . . as well as other flavor ingredients such as thymol, menthol, eucalyptol, methyl salicylate, and the like which are difficult to dissolve or emulsify in the aqueous/alcoholic carrier without the use of surfactants. Moreover, these flavor oils can impart turbidity and bitterness to the liquid oral composition.

U.S. Pat. No. 3,164,524 describes oral antiseptic compositions comprising an aqueous alcoholic solution containing menthol, methyl salicylate, thymol and eucalyptol. These compositions further comprise benzoic acid, boric acid and 2,2-thiobis-(4,6-dichlorophenol). Although having highly effective antiseptic properties, these compositions are known to have a relatively unpleasant bitter and biting taste.

U.S. Pat. No. 4,945,087 describes compositions containing thymol in which the unpleasant or harsh taste of thymol has been masked by the presence of a sugar alcohol and an effective amount of anethole. These compositions can also contain eucalyptol, menthol, benzoic acid, methyl salicylate and other optional ingredients.

U.S. Pat. No. 3,867,262 discloses a process for the preparation of terpeneless essential oils whereby the oil is distilled to remove non-volatile materials. The volatile components are adsorbed onto a solid alumina adsorbant which has been pre-treated with ethyl acetate to alter the relative affinity of the adsorbant for the terpenes and for the oxygenated components of the oil. The terpenes are separated from the desired constituents of the oil by elution of the adsorbant with a terpenephilic solvent.

U.S. Pat. No. 5,030,459 describes chewing gum compositions which contain a deterpenated and fractionated flavor oil for better flavor impact, greater sustained flavor release and improved taste. These compositions are solid chewing gum compositions and do not inlcude liquid oral compositions such as mouthwashes and cough syrups.

Because of the problems of turbidity and bitterness associated with the incorporation of flavor oils in liquid oral products, a need exists for flavor oils which have improved taste and a reduction or elimination of turbidity. It is an object of the present invention to provide liquid oral composition comprising flavor oil having improved taste and turbidity characteristics. It is a further object of this invention to provide liquid oral compositions, such as mouthwashes, sprays, rinses, cough syrups and the like, which have incorporated therein deterpenated and fractionated flavor oils. It is an even further object of the present invention to provide liquid oral compositions containing deterpenated and fractionated flavor oils which are non-bitter and non turbid. More specifically, it is an object of this invention to provide improved liquid oral compositions containing deterpenated and fractionated flavor oils wherein the monoterpenes and sesquiterpenses have been removed.

SUMMARY OF THE INVENTION

This invention relates to improved liquid oral compositions comprising a liquid carrier and one or more deterpenated and fractionated flavor oil(s). The compositions of this invention includes for example, mouthwashes, mouth rinses, sprays, cough syrups and the like. The flavor oils are preferaby any of the essential oils such as, for example peppermint oil, spearmint oil, eucalyptus oil, lemon oil, orange oil, thyme oil, origanum oil and the like. More preferably the flavor oils are mint oils, such as peppermint, spearmint and corn mint (mentha arvensis). The flavor oils of this invention are deterpenated and fractionated by vacuum distillation or by a spinning band column to remove the "heads" and "tails" of the oils which are comprised primarily of terpenes such as monoterpenes and sesquiterpenes. The deterpenated and fractionated flavor oils are incorporated into liquid oral composition in amounts ranging from aoubt 0.001% to about 5% by weight of said composition. The compositions of the present invention do not exhibit bitterness and turbidity in comparision to compositions containing flavor oil which are not deterpenated and fractionated in accordance with this invention. The liquid carrier can be water, alcohol or mixtures thereof.

DETAILED DESCRIPTION

The compositions of the present invention are liquid oral compositions comprising a liquid carrier and one or more deterpenated and fractionated flavor oil(s). The compositions include, for example, mouthwashes, mouth rinses, mouth sprays, cough syrups, liquid cold and flu medications, elixirs, beverages and the like. Oral compositions used herein means any compostion which is ingested or otherwise placed in the oral cavity.

The compositions of this invention comprise a liquid carrier. The liquid carrier can constitute up to about 99.999% by weight of said composition. The liquid carrier can be any dietary or pharmaceutically acceptable liquid known in the art. Preferably the liquid carrier comprises water, alcohol or mixtures thereof. More preferably, the liquid carrier comprises about 5% to about 30% by volume ethanol and about 70% to about 90% by volume water.

The compositions of this invention contain one or more deterpenated and fractionated flavor oil(s). The flavor oil or mixtures thereof preferably comprise from about 0.001% to about 5% by weight of the composition. Preferably, the flavor oils are any and all essential types of oils, such as, for example, lemon oil, lime oil, orange oil, grapefruit oil, peppermint oil, spearmint oil, corn mint oil, thyme oil, origanum oil, oil of bay, oil of bergamot, and the like. The preferred essential oils are selected from the group consisting of mint oils such as peppermint, spearmint and corn mint and mixtures thereof.

The flavor oil that is incorporated into the compositions of this invention has been fractionated or rectified using standard distillation and/or extraction equipment to remove both the "low end" and "high end" terpene components. This can be carried out through standard distillation procedures using a vacuum distillation apparatus or a spinning band column. Terpenes themselves are simple, non-saponifiable hydrocarbons which are multiples of the isoprene molecule ($C_5H_8$) whose molecular formula (I) is set forth below.

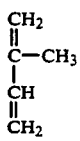

Monoterpenes (II) are basically comprised of two of the above isoprene units whereas sesquiterpenes (III) are comprised of three of these units.

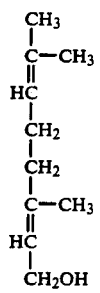

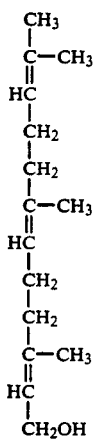

An additional type of fractionation of peppermint oil can be done by extensive distillation or rectification whereby more of the head and tail as well as specific middle fractions were removed. Repeated distillations in this manner removes not only the mono- and sesquiterpenes but the menthonic fraction as well in a number of the mint flavor oils.

The major constituents of the "menthonic" fraction are menthone, its isomer iso-menthone, and menthofuran. Menthone has been traditionally understood to be an essential component of peppermint oil. Reducing the oil to more than 50% of the menthone and iso-menthone content as well as removal of the major portion of menthofuran has resulted in an improved quality oil. The improved oil possessed a clean mentholic sensation without the heavy herbal and resinous character. The oil had a reduced bitter taste and it would appear that the removed menthonic fraction and the tail fraction seem to contribute to the unpleasant bitter taste of peppermint.

Flavoring oils of particular utility in the practice of the present invention are those of the mint variety such as peppermint, spearmint and corn mint (mentha arvensis). The amount of deterpenated flavor oil employed is normally a matter of preference but it has been found that amounts ranging from approximately 0.001% to approximately 5.0% by weight of the final composition are preferred. The mint oils of the present invention can be utilized as the sole flavorant or can be combined with other standard mint oils and flavorants.

In a preferred embodiment of this invention, the composition is an antiseptic mouthwash. Antiseptic mouthwashes have been in widespread use for many years for general oral hygiene since their antibacterial activity enables them to control the number of bacteria present in the mouth and throat. A major disadvantage of antiseptic mouthwashes, however, is their relatively harsh and unpleasant taste. A preferred antiseptic mouthwash for use according to this invention is one that has been widely used for many years comprising an aqueous alcoholic solution of menthol, methyl salicylate, thymol and eucalyptol flavorants in combination with added coloring agents and other optional ingredients. By using one or more of the deterpenated and fractionated flavor oils of this invention in lieu of or in addition to essential oils containing the flavorants listed above, the taste and clarity of the antiseptic mouthwash is significantly improved. A more preferred embodiment of the antiseptic mouthwash composition comprises, based on total weight of said composition, about 0.05-0.15% eucalyptol, about 0.01-0.10% thymol, about 0.01-0.10% methyl salicylate and about 0.005-0.2% of one or more deterpenated and fractionated mint oil(s) of this invention.

The use of deterpenated and fractionated peppermint oil is most preferred instead of or in addition to menthol or standard peppermint oil. The deterpenated and fractionated peppermint oil provides a pleasant minty taste, whereas standard peppermint oils have the disadvantage of insolubility and reduced stability. The deterpenated and fractionated peppermint oil of this invention exhibits reduced bitterness, improved clarity, pleasant taste and improved stability.

The preferred deterpenated mint oil for use in this invention is peppermint oil comprising about 48% to about 65% L-menthol. More preferably the peppermint oil comprises about 0.11% or less L-Limonene; about 0.37% or less 1,8-cineole; about 0.08% or less cis-ocimene; about 0.2% or less G-terpinene; about 0.14% or less terpinolene; about 0.14% or less 3-octanol; about 0.11% or less 1-octen-3-ol; about 10.8 to 23.1% L-menthone; about 0.5 to 2% menthofuran; about 5.15 to 7.54% menthyl acetate; about 5 to 6.48% neo-menthol; about 48 to 65% L-menthol; and about 0.7% or less germacrene-D.

Another preferred embodiment of this invention comprises an oral liquid composition comprising thymol, an effective amount of a mixture of anethole and sugar alcohol to mask the taste of thymol, and one or more deterpenated and fractionated flavor oil(s) of this invention. These compositions preferably contain a ratio of sugar alcohol to thymol from about 333:1 to about 1000:1 and a ratio of anetholé to thymol of about 0.2:1 to about 0.5:1. Generally, the sugar alcohol is present in amounts of about 20 to about 55% by total weight of the composition. The sugar alcohols can be any of those known in the art which have effective sweetening capabilities, such as sorbitol, xylitol, mannitol, maltitol, hydrogenated starch hydrolysate and mixtures thereof. Thymol is present in the composition at a preferred level of about 0.01-0.1% by weight of the composition. Anethole preferably comprises about 0.01-0.04% by weight of the total composition.

The most preferred embodiment of this invention is a liquid mouthwash composition comprising (a) about 0.02-0.1% by weight of thymol; (b) about 20 to about 55% by weight of a sugar alcohol; (c) about 0.01 to about 0.035% by weight of anethole; (d) about 0.04 to about 0.12% by weight of eucalyptol; (e) about 0.02 to about 0.07% by weight of deterpenated and fractionated mint oil; (f) about 0.05 to about 0.25% by weight of benzoic acid; (g) about 0.02 to about 0.09% by weight of methyl salicylate; (h) about 5 to about 35% by weight of ethanol; and (i) optionally, about 0.05 to about 0.8% by weight of a surfactant; wherein the unpleasant taste of said thymol is masked by said sugar alcohol and said anethole, and wherein said percents by weight are based on the total weight of the composition.

The liquid oral compositions of this invention may also contain surface active agents or surfactants in amounts up to about 5% and fluorine-providing compounds in amounts up to about 2% by weight of the preparation. Surface active agents (surfactants) are organic materials which aid in the complete dispersion of the preparation throughout the oral cavity. The organic surface active material may be anionic, non-ionic, ampholytic, or cationic. Suitable anionic surfactants are water-soluble salts of higher fatty acid monoglyceride monosulfates, such as the sodium salt of the monosulfated monoglyceride of hydrogenated coconut oil fatty acids; higher alkyl sulfates, such as sodium lauryl sulfate; alkyl aryl sulfonates, such as sodium dodecyl benzene sulfonate; higher alkyl sulfonacetates; higher fatty acid esters of 1,3-dihydroxy propane sulfonates; and substantially saturated higher aliphatic acyl amides of lower aliphatic amino carboxylic acids such as those having 12 to 16 carbons at the fatty acid, alkyl or acyl radicals. Examples of the last mentioned amides are N-lauroyl sarcosine, and the sodium, potassium, and ethanolamide salts of N-lauroyl, N-myristyl or N-palmitoyl sarcosine.

The non-ionic surfactants employed are poly(oxyethylene)-poly(oxypropylene) block copolymers. Such copolymers are known commercially as Poloxamers and are produced in a wide range of structures and molecular weights with varying contents of ethylene oxide and propylene oxide. The non-ionic Poloxamers according to the invention are non-toxic and acceptable as direct food additives. They are stable and readily dispersible in aqueous systems and are compatible with a wide variety of formulating ingredients for oral preparations. These surfactants should have an HLB (Hydrophilic-Lipophilic Balance) of between about 10 and 30 and preferably between 10 and 25.

Thus, non-ionic surfactants useful in this invention include Poloxamers:

| | | |
|---|---|---|
| 105 | 188 | 284 |
| 108 | 215 | 288 |
| 123 | 217 | 334 |
| 124 | 234 | 335 |
| 183 | 235 | 338 |
| 184 | 237 | 407 |
| 185 | 238 | |

Generally these polymers should constitute from 0.2% to 2% by weight of total volume of liquid oral preparation (% w/v) and preferably from 0.5% to 1% w/v. A particularly preferred Poloxamer is Poloxamer 407 having an HLB of about 22. Such a polymer is sold under the trademark Pluronic F-127 (BASF-WYANDOTTE CORP.).

Another class of non-ionic surfactants useful in this invention are ethoxylated hydrogenated castor oils. Such surfactants are prepared by hydrogenating castor oil and treating the so-formed product with from about 10 to 200 moles of ethylene glycol. They are designated as PEG (numeral) hydrogenated castor oil in accordance with the Dictionary of the Cosmetics, Toiletries and Fragrance Association, 3rd Ed. wherein the numeral following PEG indicates the degree of ethoxylation, i.e. the number of moles of ethylene oxide added. Suitable PEG hydrogenated castor oils include PEG 16, 20, 25, 30, 40, 50, 60, 80, 100 and 200. The ethoxylated hydrogenated castor oils are used in the same concentrations as the above described poly(oxyethylene)-poly(oxypropylene) block copolymers.

Other non-ionic surface active agents which may be suitable include codensates of sorbitan esters of fatty acids with from 20 to 60 moles of ethylene oxide (e.g., "Tweens" a trademark of ICI United States, Inc.), and amphoteric agents such as quaternized imidazole derivatives.

Additional non-ionic surfactants which may be suitable are the condensation products of an alpha-olefin oxide containing 10 to 20 carbon atams, a polyhydric alcohol containing 2 to 10 carbons and 2 to 6 hydroxyl groups and either ethylene oxide or a heteric mixture of ethylene oxide and propylene oxide. The resultant surfactants are polymers having a molecular weight in the range of 400 to about 1600 and containing 40% to 80% by weight of ethylene oxide, with an alpha-olefin oxide to polyhydric alcohol mole ratio in the range of about 1:1 to 1:3.

Cationic surface active agents which may be suitable are molecules that carry a positive charge such as cetylpyridinium chloride.

Fluorine providing compounds may be present in the oral preparations of this invention. These compounds may be slightly water soluble or may be fully water soluble and are characterized by their ability to release fluoride ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid preparation such as a mouthwash, the fluorine providing compound is generally present in an amount sufficient to release up to about 0.15%, preferably about 0.001% to about 0.1% and most preferably from about 0.001% to about 0.05% fluoride by weight of the preparation.

If desired, auxiliary sweeteners may be utilized in the compositions of the invention. Those sweeteners which may be included are those well known in the art, inlcuding both natural and artificial sweeteners.

The sweetening agent (sweetener) used may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof. Without being limited to particular sweeteners, representative illustrations encompass:

A. Water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. Water-soluble artificial sweeteners such as the soluble saccharin salts, i.e. sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. Dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerine and L-aspartyl-L-2,5,dihydrophenyl-glycine, L-aspartyl-2,5-dihydro-L-phenylalanine; L-aspartyl-L-(1-cyclohexyen)alanine; and the like;

D. Water-soluble sweeteners derived from naturally occurring water-soluble sweeteners, such as a chlorinated derivative of ordinary sugar (sucrose), known, for example, under the product description of sucralose; and E. Protein based sweeteners such as thaumatoccous danielli (Thaumatin I and II).

In general, an effective amount of auxiliary sweetener is utilized to provide the level of sweetness desired for a particular composition, and this amount will vary with the sweetener selected.

The compositions of this invention may also contain coloring agents or colorants. The coloring agents are used in amounts effective to produce the desired color. The coloring agents (colorants) useful in the present invention, include the pigments such as titanium dioxide, which may be incorporated in amounts of up to about 2% by weight of the composition, and preferably less than about 1% by weight. Colorants may also include natural food colors and dyes suitable for food, drug and cosmetic applications. These colorants are known as F.D. & C. dyes. The materials acceptable for the foregoing spectrum of use are preferably water-soluble, and include indigoid dye, known as F.D. & C. Blue No. 3, which is the disodium salt of 5,5-indigotindisulfonic acid. Similarly, the dye known as Green No. 1 comprises a triphenylmethane dye and is the monosodium salt of 4-[4-N-ethyl-p-sulfobenzylamino)diphenylmethylene]-[1-M-ethyl-p-sulfoniumbenzyl) 2,5-cyclohexadienimine]. Additional examples include the yellow dye, known as D&C Yellow No. 10, and the dye known as F.D.& C. Green No. 3 which comprises a triphenylmethane dye.

In general, the compositions of this invention are prepared utilizing techniques well known to those skilled in the art. Thus, the liquid compositions may be prepared by mixing the alcohol soluble ingredients with ethanol, adding a quantity of water to the mixture thus obtained, and then blending or mixing in the water soluble ingredients. For example, in preparing one liter of a typical liquid oral composition, thymol, eucalyptol, and deterpenated and fractionated mint oil, methyl salicylate, anethole, surfactant, and benzoic acid are dissolved in and mixed with ethanol. To this resulting mixture a sufficient quantity of water is added, and then the auxiliary sweetener, water soluble colorants, buffers, and other optional ingredients and the like are blended in. Then additional water is added to make up one liter.

Those skilled in the art will appreciate that the total amount of all ingredients (components) used in the compositions of this invention equals 100% by weight of the total composition. Also, unless stated otherwise, all percents herein are percent by weight of the total composition.

The liquid oral compositions of this invention containing the deterpenated and fractionated flavor oil have improved taste and clarity. Compositions containing the deterpenated and fractionated flavor oils have significantly less bitterness than compositions having standard terpene-containing flavor oils. Additionally, the deterpenated and fractionated flavor oils of this invention result in liquid compositions having improved clarity and substantially no turbidity. The deterpenated and fractionated flavor oils are more hydrophillic and are easily dissolved in water or a water/alcohol mixture. Thus, significantly less surfactant is required to dissolve the flavor oil and to maintain a stable solution.

The following examples are presented to further demonstrate this invention. The examples are intended to be illustrative and are not intended in a limitative sense. All parts and percentages given are on a weight basis unless otherwise indicated.

The peppermint oils used in the follwing examples were shown by gas chromatagraphic analyses to have the composition shown in Table I below:

TABLE I

| Peppermint oil: | A | B | C | D |
| --- | --- | --- | --- | --- |
| Component (%) | | | | |
| Isobutyraldehyde | 0.04 | 0 | 0 | 0 |
| Isovaleraldehyde | 0.19 | 0 | 0 | 0 |
| A-Pinene | 0.73 | 0.10 | 0 | 0 |
| B-Pinene | 0.95 | 0.25 | 0 | 0 |
| Sabinene | 0.45 | 0.12 | 0 | 0 |
| Myrcene | 0.20 | 0.07 | 0 | 0 |
| A-Terpinene | 0.34 | 0 | 0 | 0 |
| L-Limonene | 1.49 | 0.68 | 0.11 | 0 |
| 1,8-Cineole | 4.64 | 2.89 | 0.37 | 0 |
| Cis-Ocimene | 0.30 | 0.17 | 0.08 | 0 |
| G-Tepinene | 0.68 | 0.54 | 0.20 | 0 |
| P-Cymene | 0.18 | 0.15 | 0 | 0 |
| Terpinolene | 0.15 | 0.11 | 0.14 | 0 |
| 3-Octanol | 0.24 | | 0.14 | |
| 1-Octen-3-ol | 9.17 | 0.17 | 0.11 | 0 |
| trans-Sabinese Hydrate | 1.04 | 0.12 | 1.04 | 0.18 |
| L-Menthone | 19.33 | 22.28 | 23.13 | 10.84 |
| Menthofuran | 1.84 | 1.95 | 2.02 | 0.50 |
| Iso-menthone | 2.63 | 3.11 | 3.30 | 2.04 |
| B-Bourbonene | 0.45 | 0.43 | 0.35 | 0.61 |
| Linalool | 0.22 | 0.18 | 0.23 | 0.32 |
| Menthyl Acetate | 5.14 | 4.59 | 5.15 | 7.54 |
| Neo-menthol | 4.04 | 5.75 | 5.04 | 6.48 |
| B-Caryophyllene | 1.62 | 1.37 | 0.89 | 2.07 |
| Terpinen-4-ol | 1.13 | 1.62 | 1.43 | 1.05 |
| L-Menthol | 41.11 | 46.87 | 51.35 | 63.57 |
| Pulegone | 1.25 | 1.48 | 1.09 | 1.63 |
| Germacrene-D | 2.12 | 1.92 | 0.37 | 0.70 |
| Piperitone + | 0.99 | 0.62 | 0.64 | 0.92 |

TABLE I-continued

| Peppermint oil: | A | B | C | D |
|---|---|---|---|---|
| Viridiflorol | 0.37 | 0.10 | 0.18 | 0 |

A = Standard peppermint oil
B = Moderately fractionated peppermint oil
C = Deterpenated and highly fractionated peppermint oil
D = Deterpenated and specially fractionated peppermint oil with lower menthone fraction

EXAMPLE I

Four (4) samples of liquid oral compositions within the scope of the present invention were prepared with varying amounts of surfactant according to the following procedure.

200 ml of ethanol were added to 1 gram of peppermint oil C. To 400 ml of distilled water are added 1.25, 3.0, 6.0 and 9.0 grams, respectively of Pluronic 127 surfactant (polyoxyalkylene derivatives of propylene glycol available from BASF-Wyandotte Corp.). The ethanol/peppermint oil components above were added to the respective water/surfactant components above while mixing rapidly. Each sample was diluted to 1 liter with distilled water. The compositions had a relatively non-bitter, minty taste. Similar results would be obtained using peppermint oil D.

EXAMPLE II

Comparative

Four (4) samples of liquid oral compositions falling outside the scope of this invention were prepared following the procedures of Ex. I except that the deterpenated and fractionated peppermint oil C was replaced with standard peppermint oil A. The compositions had a relatively bitter minty taste.

EXAMPLE III

Comparative

Four (4) samples of liquid oral compositions falling outside the scope of this invention were prepared following the procedures of Ex. I, except that the deterpenated and fractionated peppermint oil C was replaced with moderately fractionated peppermint oil B. The compositions had a clean minty taste.

EXAMPLE IV

The compositions prepared in Examples I, II and III above were evaluated for appearance in turbidity. The appearance was evaluated by visual observation. Turbidity was evaluated using a spectrophotometer at nephlometric angle 90° measurement ratioed to sum of transmitted light and forward scatter light measurement. The results are presented in Table II below.

TABLE II

| Surfactant Concentration (g./liter) | National Turbidity Unit (Appearance) EXAMPLE: | | |
|---|---|---|---|
| | I | II | III |
| 1.25 | 2.8 (clear) | 13.8 (cloudy) | 3.3 (slightly hazy) |
| 3.0 | 2.2 (clear) | 2.9 (slightly hazy) | 2.9 (slightly hazy) |
| 6.0 | 2.1 (clear) | 2.7 (clear) | 3.1 (slightly hazy) |
| 9.0 | 2.1 (clear) | 2.7 (clear) | 3.2 (slightly hazy) |

We claim:

1. A liquid oral composition wherein all of the components are in liquid form comprising a liquid carrier and a peppermint oil comprising about 0.11% or less L-Limonene; about 0.37% or less 1,8-cineole; about 0.08% or less cis-ocimene; about 0.2% or less G-terpinene; about 0.14% or less terpinolene; about 0.14% or less 3-octanol; about 0.11% or less 1-octen-3-ol; about 10.8 to 23.1% L-methone; about 0.5 to 2% menthofuran; about 5.15 to 7.54% menthyl acetate; about 5 to 6.48% neo-menthol; about 48 to 65% L-menthol; and about 0.7% or less germacrene-D.

2. The composition of claim 1 wherein said liquid carrier is selected from the group consisting of water, alcohol or mixture thereof.

3. The composition of claim 2 wherein said liquid carrier comprises about 5 to about 30% by volume ethanol and about 70 to about 90% by volume water.

4. The composition of claim 1 wherein said essential oil further contains flavorants selected from the group consisting of menthol, thymol, eucalyptol, methyl salicylate and mixtures thereof.

5. The composition of claim 1 wherein said composition is an antiseptic mouthwash further comprising based on total weight of said composition about 0.05 to 0.15% eucalyptol, 0.01 to 0.10% thymol, 0.01 to 0.10% methyl salicylate.

* * * * *